(12) United States Patent
Burton, II

(10) Patent No.: US 10,762,629 B1
(45) Date of Patent: Sep. 1, 2020

(54) SEGMENTING MEDICAL IMAGES

(71) Applicant: Seg AI LLC, Denver, CO (US)

(72) Inventor: William Stewart Burton, II, Denver, CO (US)

(73) Assignee: SegAI LLC, Denver, CO (US)

(*) Notice: Subject to any disclaimer, the term of this patent is extended or adjusted under 35 U.S.C. 154(b) by 0 days.

(21) Appl. No.: 16/803,423

(22) Filed: Feb. 27, 2020

Related U.S. Application Data

(60) Provisional application No. 62/935,165, filed on Nov. 14, 2019.

(51) Int. Cl.
*G06T 7/00* (2017.01)
*G06T 7/174* (2017.01)
*G06T 7/11* (2017.01)

(52) U.S. Cl.
CPC .............. *G06T 7/0012* (2013.01); *G06T 7/11* (2017.01); *G06T 7/174* (2017.01); *G06T 2207/10088* (2013.01); *G06T 2207/20081* (2013.01)

(58) Field of Classification Search
None
See application file for complete search history.

(56) References Cited

U.S. PATENT DOCUMENTS

| | | | |
|---|---|---|---|
| 8,270,696 B2 | 9/2012 | Udupa et al. | |
| 8,280,132 B2* | 10/2012 | Madabhushi | G06K 9/0014 382/128 |
| 9,972,092 B2 | 5/2018 | Lin et al. | |
| 2018/0025512 A1* | 1/2018 | Zhu | G06T 11/006 382/131 |
| 2018/0218497 A1 | 8/2018 | Golden et al. | |
| 2018/0225823 A1 | 8/2018 | Zhou et al. | |
| 2019/0080456 A1 | 3/2019 | Song et al. | |

(Continued)

FOREIGN PATENT DOCUMENTS

| | | |
|---|---|---|
| CN | 102289811 | 12/2011 |
| CN | 106780518 | 5/2017 |

(Continued)

OTHER PUBLICATIONS

Chen, et al., "Blazingly Fast Video Object Segmentation with Pixel-Wise Metric Learning", Computer Vision Foundation, Apr. 9, 2018, 11 pgs.

Oh, et al., "Fast User-Guided Video Object Segmentation by Interaction-and-Propagation Networks", arXiv:1904.09791v2, May 2, 2019, 10 pgs.

(Continued)

*Primary Examiner* — Fayyaz Alam
(74) *Attorney, Agent, or Firm* — Henry Patent Law Firm PLLC

(57) ABSTRACT

In a general aspect, medical images are segmented by a medical image segmentation system. In some aspects, a medical image segmentation method includes obtaining a medical image comprising a series of images; obtaining a surrogate context based on a support set of images; identifying a query set of images; providing the surrogate context, the support set of images and the query set of images as inputs to a machine learning process; and segmenting the query set by operation of the machine learning process executed on a computer system, wherein executing the machine learning process produces segmentation information of the query set. The support set of images includes a first subset of the series of images and the query set of images includes a second subset of the series of images.

30 Claims, 6 Drawing Sheets

(56) References Cited

U.S. PATENT DOCUMENTS

| | | | |
|---|---|---|---|
| 2019/0205606 A1 | 7/2019 | Zhou et al. | |
| 2019/0223725 A1 | 7/2019 | Lu et al. | |
| 2019/0244398 A1* | 8/2019 | Carmi | G06T 11/008 |
| 2019/0347802 A1* | 11/2019 | Linguraru | G06T 7/149 |
| 2020/0143934 A1* | 5/2020 | Gering | G06T 7/12 |

FOREIGN PATENT DOCUMENTS

| | | |
|---|---|---|
| CN | 107067393 | 8/2017 |
| CN | 107590813 | 1/2018 |
| CN | 107808389 | 3/2018 |
| CN | 108537803 | 9/2018 |
| CN | 108805877 | 11/2018 |
| CN | 110415253 | 11/2019 |
| EP | 3316217 | 5/2018 |
| JP | 2018195293 | 12/2018 |
| KR | 20170143293 | 3/2018 |
| WO | 2018162338 | 9/2018 |
| WO | 2018229490 | 12/2018 |

OTHER PUBLICATIONS

Rakelly, et al., "Few-Shot Segmentation Propagation with Guided Networks", UC Berkeley, May 25, 2018, 11 pgs.

Ronneberger, et al., "U-Net: Convolutional Networks for Biomedical Image Segmentation", arXiv:1505.04597v1, May 18, 2015, 8 pgs.

Roy, et al., "'Squeeze & Excite' Guided Few-Shot Segmentation of Volumetric Images", arXiv:1902.01314v2, Oct. 11, 2019, 15 pgs.

Sakinis, et al., "Interactive segmentation of medical images through fully convolutional neural networks", arXiv:1903.08205v1, Mar. 19, 2019, 10 pgs.

Shaban, et al., "One-Shot Learning for Semantic Segmentation", arXiv:1709.03410v1, Sep. 11, 2017, 17 pgs.

Wang, et al., "DeepIGeoS: A Deep Interactive Geodesic Framework for Medical Image Segmentation", arXiv:1707.00652v3, Sep. 19, 2017, 14 pgs.

Zhang, et al., "CA Net: Class-Agnostic Segmentation Networks with Iterative Refinement and Attentive Few-Shot Learning", Computer Vision Foundation, Mar. 6, 2019, 11 pgs.

* cited by examiner

SEGMENTING MEDICAL IMAGES

CROSS-REFERENCE TO RELATED APPLICATIONS

This application claims priority to U.S. Provisional Application No. 62/935,165, filed Nov. 14, 2019 and entitled "Segmenting Medical Images," which is hereby incorporated by reference.

BACKGROUND

The following description relates to segmenting medical images.

Medical images are generated by many types of imaging platforms, for example, computed tomography (CT), magnetic resonance imaging (MRI), and positron emission tomography (PET) technologies, to name a few. Medical images are often segmented to identify anatomical features of an imaging subject.

DETAILED DESCRIPTION

In some aspects of what is described here, a medical image (e.g., an image of a three-dimensional volume) is segmented by an automated process. The medical image segmentation process may identify one or more objects (e.g., anatomical features of an imaging subject) in the medical image, for example, by distinguishing objects of interest from background, noise, or other objects in the image. In some cases, the segmentation process generates a segmentation map that indicates the locations of the identified objects. In some implementations, an artificial neural network using deep learning algorithms can generate a segmentation map that corresponds to delineated objects in target images. The artificial neural network may perform a segmentation process on the target images, for example, using one or more supporting images that are adjacent to the target images and are previously segmented.

In some implementations, the systems and methods described here can provide technical advantages over, or improvements to, existing technologies. In some instances, the image segmentation techniques described here can significantly expedite the segmentation process (e.g., relative to certain manual, semi-automatic and automated segmentation methods). In some implementations, the image segmentation techniques described here can be used to segment a broader range of medical images, to identify a broader range of objects of interest within a given medical image, to segment a medical image using less training data or human input, or to provide other advantages over existing automated segmentation methods. For example, the image segmentation techniques described here, in some cases, may provide more accurate segmentation predictions and may be applied to multiple tasks without a requirement to retrain the machine learning algorithm. In some instances, the artificial neural network can be trained using any number of segmentation data sets from varying domains (e.g., natural images, different medical image modalities, etc.) without being limited to the domain of medical image segmentation. As a result, issues such as brittleness and domain shift issues that are commonly associated with classic supervised, semi-supervised, and reinforcement learning algorithms, may be addressed. In certain implementations, the systems and methods described here may be applied in applications related to manufacturing or aerospace in order to access the integrity of a material or components. In some cases, a combination of these and potentially other advantages and improvements may be obtained.

Figure 1:
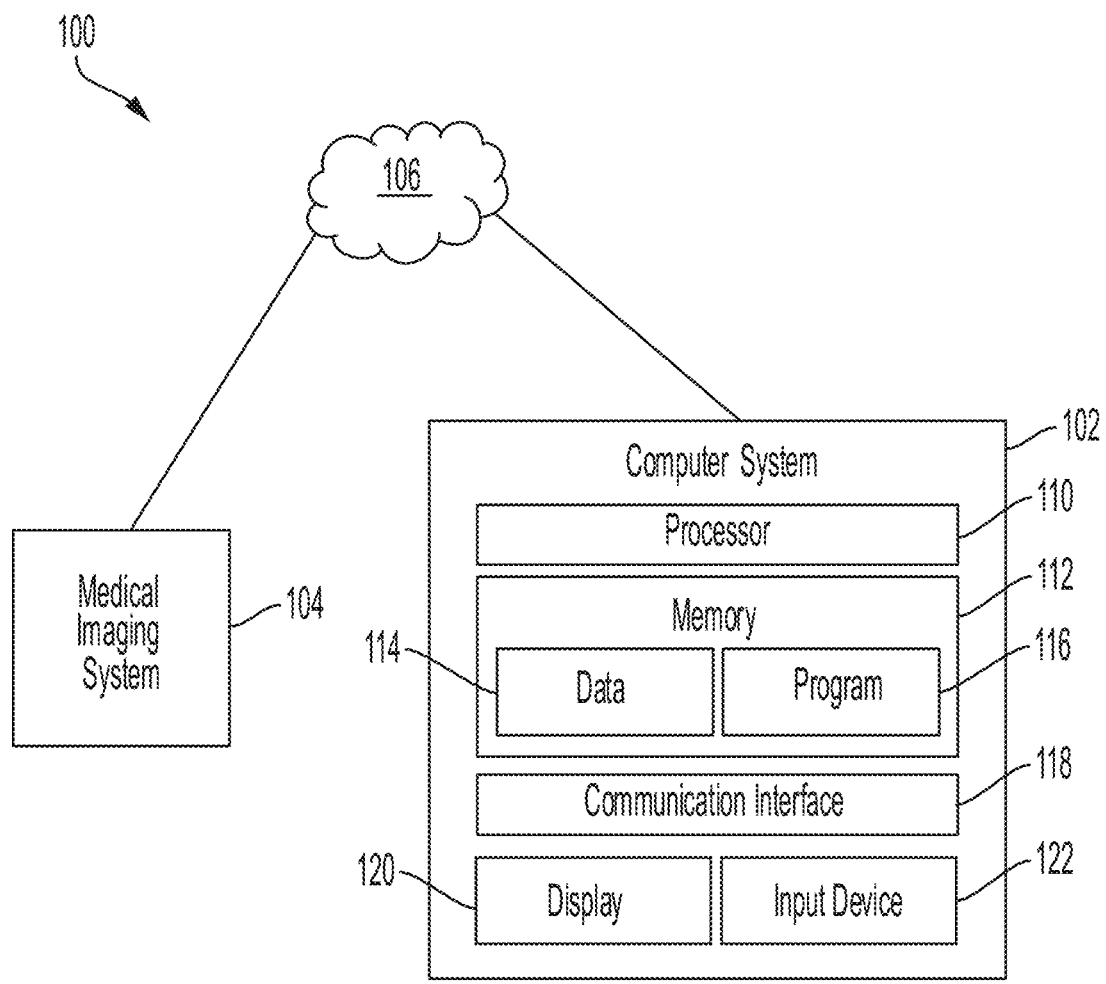
FIG. 1 is a schematic diagram of an example medical image segmentation system.

FIG. 1 is a schematic diagram of an example medical image segmentation system 100. The example system 100 includes a computer system 102, a medical imaging system 104, and a communication network 106. The image segmentation system 100 may include additional or different features.

In the example shown in FIG. 1, the computer system 102 includes a processor 110, memory 112, a communication interface 118, a display device 120, and an input device 122. The computer system 102 may include additional components, such as, for example, input/output controllers, communication links, power, etc. The computer system 102 can be used, for example, to process medical images obtained from the medical imaging system 104, which may be received by the computer system 102 directly or indirectly (e.g., through the network 106 or otherwise). For instance, the computer system 102 may be used to implement one or more aspects of the systems and techniques described with respect to FIGS. 2, 3, 4, 5 and 6, or to perform other types of operations.

The computer system 100 may include a single computing device, or multiple computers that operate in proximity or generally remote from each other and typically interact through a communication network 106, e.g. via interface 118. Examples of communication network 106 include a local area network ("LAN") and a wide area network ("WAN"), an inter-network (e.g., the Internet), a network comprising a satellite link, and peer-to-peer networks (e.g., ad hoc peer-to-peer networks).

In some implementations, the medical imaging system 104 may include any suitable type of medical imaging system. For example, the medical imaging system 104 may generate medical images based on X-ray radiography, magnetic resonance imaging (MRI), medical ultrasonography or ultrasound, endoscopy, elastography, tactile imaging, thermography, medical photography, nuclear medicine functional imaging techniques as positron emission tomography (PET) and single-photon emission computed tomography (SPECT), or another imaging technology. In some instances, the medical imaging system 104 can noninvasively acquire medical images of an imaging subject (e.g., a human subject or another type of imaging subject). In some implementations, the medical imaging system 104 may produce 2D, 3D or 4D images using any suitable technique. In some instances, the medical imaging system 104 may use volume rendering techniques to produce 3D images (e.g., images over three spatial dimensions) based on a plurality of 2D imaging scans (e.g., each of the 2D imaging scans produces a two-dimensional slice of the 3D image).

In some implementations, medical image data (e.g., 2D, 3D, or 4D medical images) collected by the medical imaging system 104 may be uploaded through the communication network 106 and stored, and the computer system 102 may then access the medical image data through the communication network 106 segmentation or other types of analysis and processing. In some other implementations, medical image data collected by the medical imaging system 104 may be directly saved in the memory 112 of the computer system 102, which may be local to or remote from the medical imaging system 104.

In some implementations, some of the processes and logic flows described in this specification can be performed by one or more programmable processors, e.g. processor 110, executing one or more computer programs to perform actions by operating on input data and generating output. For example, the processor 110 can run the programs 116 by executing or interpreting scripts, functions, executables, or other modules contained in the programs 116. In some implementations, the processor 110 may perform one or more of the operations described, for example, with respect to FIGS. 2, 3, 4, 5 and 6.

In some implementations, the processor 110 can include various kinds of apparatus, devices, and machines for processing data, including, by way of example, a programmable data processor, a system on a chip, or multiple ones, or combinations, of the foregoing. In certain instances, the processor 110 may include special purpose logic circuitry, e.g., an FPGA (field programmable gate array), an ASIC (application specific integrated circuit), or a Graphics Processing Unit (GPU) for running the deep learning algorithms. In some instances, the processor 110 may include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. In some examples, the processor 110 may include, by way of example, both general and special purpose microprocessors, and processors of any kind of digital computer.

In some implementations, the process 110 may include both general and special purpose microprocessors, and processors of any kind of quantum or classic computer. Generally, a processor 110 will receive instructions and data from a read-only memory or a random-access memory or both, e.g. memory 112. In some implementations, the memory 112 may include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. In some cases, the processor 110 and the memory 112 can be supplemented by, or incorporated in, special purpose logic circuitry.

In some implementations, the data 114 stored in the memory 112 may include medical images, segmentation maps of one or more support images, weight parameters and activations for machine learning algorithms, and output segmentation maps. In some implementations, the programs 116 can include software applications, scripts, programs, functions, executables, or other modules that are interpreted or executed by the processor 110. In some implementations, the programs 116 may include machine-readable instructions for performing deep learning algorithms. In some instances, the programs 116 may include machine-readable instructions for receiving a supporting image or automatically selecting a supporting image and performing a segmentation process on target images. In some instances, the programs 116 may obtain input data from the memory 112, from another local source, or from one or more remote sources (e.g., via a communication link). In some instances, the programs 116 may generate output data and store the output data in the memory 112, in another local medium, or in one or more remote devices (e.g., by sending the output data via the communication network 106). In some examples, the programs 116 (also known as, software, software applications, scripts, or codes) can be written in any form of programming language, including compiled or interpreted languages, declarative or procedural languages. In some implementations, the programs 116 can be deployed to be executed on one computer or on multiple computers that are located at one site or distributed across multiple sites and interconnected by the communication network 106. For instance, the programs 116 may operate in the cloud, and the computer system 102 may access the programs 116 through an Internet connection.

In some implementations, the communication interface 118 may be connected to the communication network 106, which may include any type of communication channel, connector, data communication network, or other link. In some instances, the communication interface 118 may provide communication with other systems or devices. In some instances, the communication interface 118 may include a wireless communication interface that provides wireless communication under various wireless protocols, such as, for example, Bluetooth, Wi-Fi, Near Field Communication (NFC), GSM voice calls, SMS, EMS, or MMS messaging, wireless standards (e.g., CDMA, TDMA, PDC, WCDMA, CDMA2000, GPRS) among others. In some examples, such communication may occur, for example, through a radio-frequency transceiver or another type of component. In some instances, the communication interface 118 may include a wired communication interface (e.g., USB, Ethernet) that can be connected to one or more input/output devices, such as, for example, a keyboard, a pointing device, a scanner, or a networking device such as a switch or router, for example, through a network adapter.

In some implementations, the communication interface 118 can be coupled to input devices and output devices (e.g., the display device 120, the input device 122, or other devices) and to one or more communication links. In the example shown, the display device 120 is a computer monitor for displaying information to the user or another type of display device. In some implementations, the input device 122 is a keyboard, a pointing device (e.g., a mouse, a trackball, a tablet, and a touch sensitive screen), or another type of input device, by which the user can provide input to the computer. In some examples, the computer system 102 may include other types of input devices, output devices, or both (e.g., mouse, touchpad, touchscreen, microphone, motion sensors, etc.). The input devices and output devices can receive and transmit data in analog or digital form over communication links such as a wired link (e.g., USB, etc.), a wireless link (e.g., Bluetooth, NFC, infrared, radio frequency, or others), or another type of link.

In some implementations, other kinds of devices may be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, the computer system 102 can interact with a user by sending documents to and receiving documents from a device that is used by the user; for example, by sending web pages to a web browser on a user's client device in response to requests received from the web browser.

Figure 2:
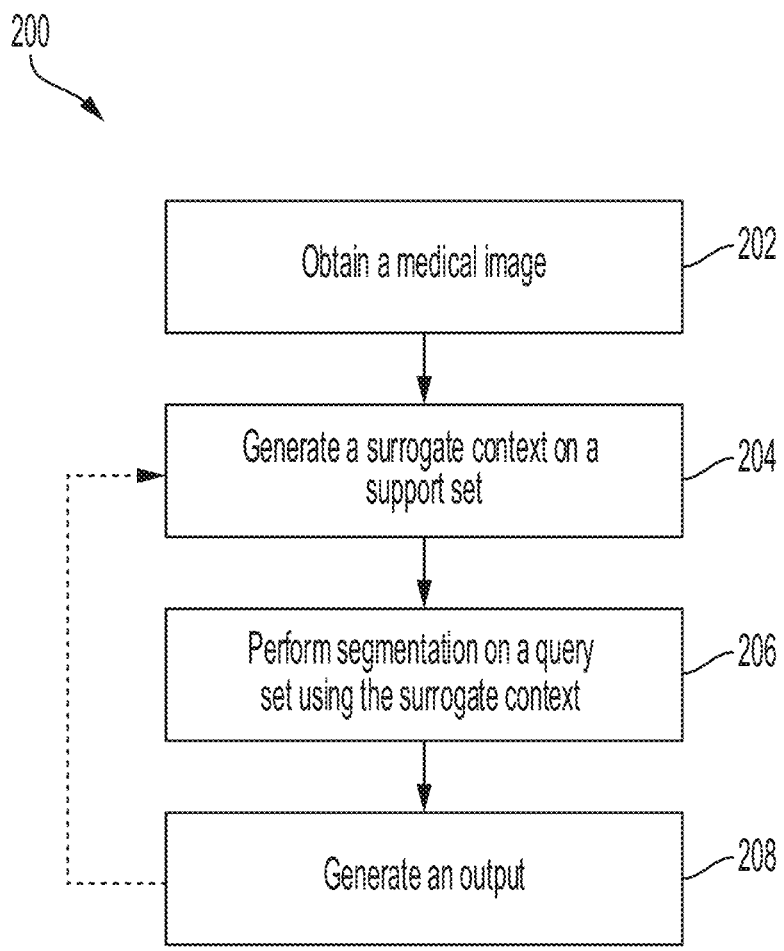
FIG. 2 is a flow chart showing an example medical image segmentation process.

FIG. 2 is a flow chart showing an example medical image segmentation process 200. In some implementations, the medical image segmentation process 200 may be an automated process used to segment medical images. The medical image segmentation process 200 may identify one or more objects (e.g., anatomical features of an imaging subject) in the medical image, for example, by distinguishing objects of interest from background, noise, or other objects in the image. For example, anatomical features may include bones, cartilage, organs, tumors, and other pathologies, as well as non-biological objects inside a body. In some cases, the segmentation process generates an output containing segmentation information that indicates the locations of the identified objects.

In some implementations, the example process 200 shown in FIG. 2 may be performed by a computer system (e.g., by the computer system 102 in FIG. 1) to segment medical images, or by another type of system. In some cases, the process 200 may be performed by a medical imaging system computer, a cloud-based computer system, a server, a server cluster, a serverless computer environment, or another type of computer system. In some examples, the process 200 can be used for segmentation of medical images generated by a medical imaging system (e.g., the medical imaging system 104 shown in FIG. 1). In some cases, the process 200 may include additional or different operations, and the operations may be performed in the order shown in FIG. 2 or in another order. In some implementations, one or more of the operations in the process 200 may be repeated or iterated, performed in parallel with other operations, or handled in another manner.

In some implementations, the image segmentation process 200 may use an artificial neural network (ANN) to generate a segmentation map that corresponds to delineated objects in target images. In some cases, the artificial neural network may perform a segmentation process on the target images, for example, using one or more supporting images that are adjacent to the target images and have been previously segmented.

At 202, a medical image is obtained. In some implementations, the medical image may include any type of medical images generated by a medical imaging system (e.g., the medical imaging system 104 as shown in FIG. 1). In some cases, the medical image is obtained by a computer system from a medical imaging system. In some implementations, the medical image may be imported directly from the medical imaging system and stored in the computer system, e.g., the computer system 102 of the medical image segmentation system 100 as shown in FIG. 1. In some implementations, the medical image may be imported through a communication network (e.g., the communication network 106 as shown in FIG. 1). In some cases, the medical image may be imported from a remote database, a local database, or a storage medium, through a communication network or obtained in another manner.

In some cases, the medical image obtained at 202 may include a series of related medical images, for example, a series of 2D images (e.g., slices) representing a 3D volume or a time series. In some examples, the series of slices may be collected with the aim of segmenting or delineating a specific structure or region of an imaging subject.

At 204, a surrogate context is generated. In some cases, in order to generate the surrogate context, a support set may be first selected from the medical image obtained at 202. In some examples, the support set is a subset of the series of images in the medical image, e.g., at least one slice from a series of slices. In some implementations, selection of the support set is performed automatically, for example, according to predetermined criteria. In some cases, a support set may be selected as the slice or slices directly adjacent to a query set, which may include another subset of the series of images in the medical image. In some cases, a support set may be determined by comparing a query set to a group of support sets according to a pre-determined similarity metric. For example, the pre-determined similarity metric may be the mean pixel-wise L2 distance, a difference between the principle components, or another quantitative metric for describing the similarity between two slices. In some cases, a support set is selected automatically, semi-automatically or manually.

In some cases, the surrogate context is generated by performing segmentation or another type of identification process on the support set, for example, to identify a structure in the support set. In some cases, the surrogate context of a support set may include one or more of a segmentation map, a contour map, an extracted feature (e.g., from edge detection), a key point map (e.g., a key structure), an annotation (e.g., scribbles and point clicks), coordinates of point clicks, or another format. In some implementations, a manual or a semi-automatic identification process may be used to generate a surrogate context (e.g., a key point map, an annotation map, or coordinates of point clicks). In certain implementations, computer vision may be used to automatically generate a surrogate context (e.g., an extracted feature).

In some implementations, a surrogate context may include a matrix of pixels (e.g., an image) with a subset of pixels. In certain implementations, the subset of pixels may represent a segmented region (e.g., in a segmentation map), a boundary (e.g., in a contour map), a feature (e.g., in an extracted map or in a segmentation map), or identified locations (e.g., in a key point map, and an annotation map). In some implementations, a segmentation map may include a matrix, in which "1"s represent one or more regions of interest in an image. In some examples, a matrix in a segmentation map may include other integers, e.g., 2, 3, 4, . . . , representing different classes or regions in an image. In some examples, a segmentation map may be a class-agnostic segmentation map, in which the integers, e.g., 0, 1, 2, 3, . . . , in a segmentation map is temporarily assigned to a region or a feature. For example, while an integer "1" representing class 1 may be assigned to an anatomy in a first slice, the anatomy in a distinct second slice may be labeled using a different integer (e.g., "2") representing class "2" in the second slice, and the integer "1" may be used to label a different anatomy in the second slice.

In some implementations, a contour map may include a matrix, in which "1"s represent a boundary of a region of interest. In some implementations, a key point map may include a matrix of pixels representing one or more locations identified by a user in an image. For example, a key point map may include a matrix, in which "1"s represent locations (e.g., pixels) in the image that are identified (e.g., clicked) by a user. For example, an annotation map may include a matrix, in which "1"s represent locations (e.g., pixels) in the image that are identified (e.g., drawn) by a user.

In some examples, the surrogate context may be used to represent a delineation of a region of interest (ROI) in a slice (e.g., delineated from other ROIs, the background, etc.). In some instances, the ROI may be designated as a distinct foreground delineated from a background. In some examples, the formats of a surrogate context may be in represented in 2D or higher dimensions such as 3D or 4D, or a combination thereof. In some cases, a surrogate context may include additional temporal or image modality dimensions.

Figure 3:
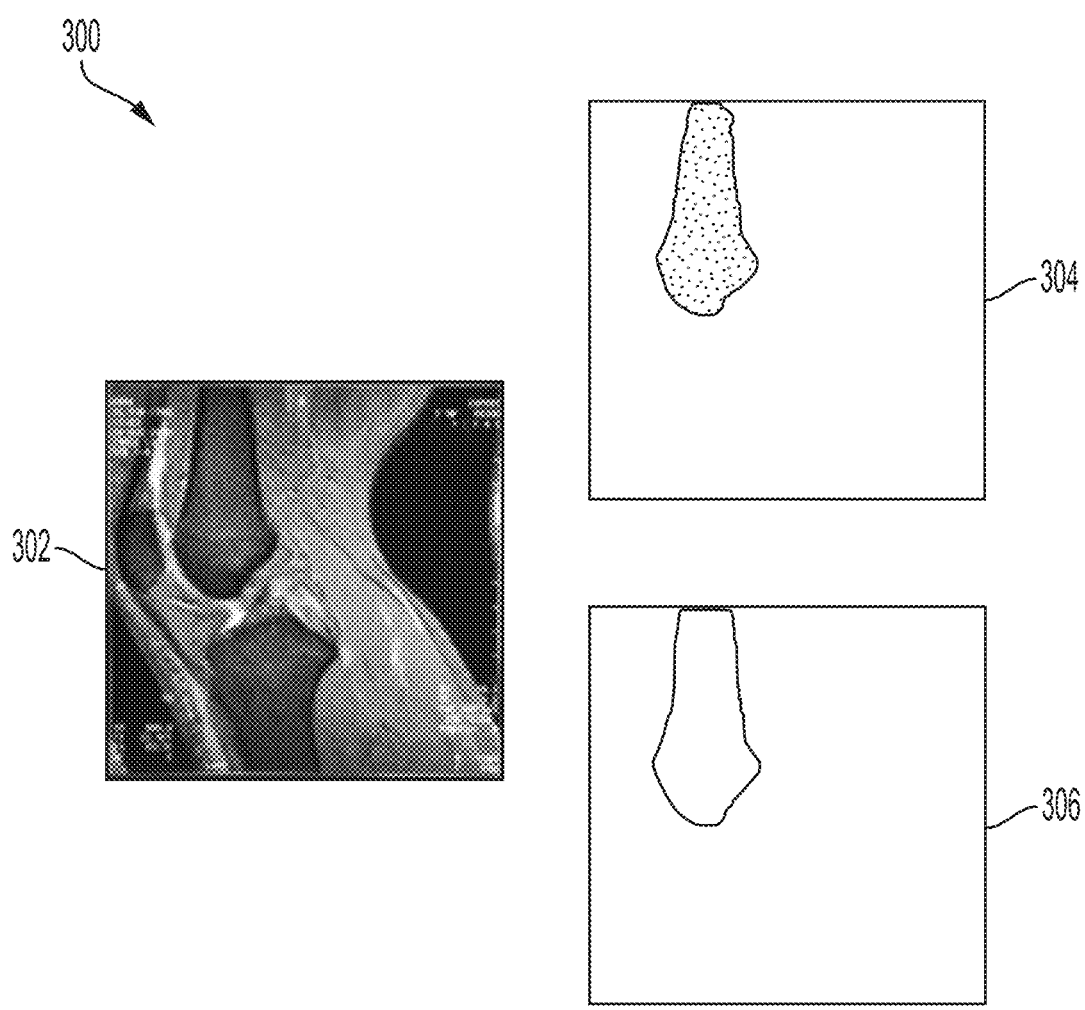
FIG. 3 shows an example medical image and a surrogate context used in the medical image segmentation process 200 shown in FIG. 2.

FIG. 3 shows an example of a medical image 302 and a surrogate context of the medical image 302 used in the medical image segmentation process 200 shown in FIG. 2. In the example shown in FIG. 3, the surrogate context may be a segmentation map 304, or a contour map 306. The example medical image 302 was obtained by Magnetic Resonance Imaging (MRI) on a human subject. The image shown in FIG. 3 is a two-dimensional image of a human knee, and the medical image 302 may include additional two-dimensional images and data. For example, the image shown in FIG. 3 may represent a single slice of a volumetric image of the human knee. The example segmentation map 304 shown in FIG. 3 denotes a region of the medical image 302 that represents a femur in a human knee. Additional or different types of anatomical features may be denoted by a segmentation map. For instance, the segmentation map 304 could include a first region representing the femur and a second region representing the tibia or another object of interest. The example contour map 306 shown in FIG. 3 denotes the same region of the medical image 302 as the segmentation map 304. Whereas the segmentation map 304 indicates the full area of the femur in the medical image 302, the contour map 306 represents the perimeter of the femur. Additional or different types anatomical features may be denoted by a contour map.

In some implementations, the surrogate context of the support set may be generated, for example by a manual annotation method, a semi-automatic method, or another type of process. In some examples, a semi-automatic method may include techniques such as, for example thresholding, hole filling, or using an artificial neural network. In some cases, an artificial neural network may take user annotations of a structure of interest as inputs for generating a surrogate context, e.g., predicting a segmentation map.

At 206, a segmentation process is performed on a query set using the surrogate context. In some implementations, the segmentation process may be applied to a query set, which may contain the remaining scans in the medical image that are not included in the support set. In some examples, the support and query sets are obtained from the same or different scans. In some cases, the support and query sets may be obtained from separate, distinct medical images with different image modalities. In some instances, the support and query sets may be determined using an automatic method, such as using a similarity metric. In some examples, the surrogate context, the support set and the query set are provided as inputs to a machine learning process to perform the segmentation process.

In some implementations, the segmentation map of the support set may be used as the surrogate context to support the segmentation process on the query set in the same scan. Since segmentation maps of two adjacent or nearby slices within a scan may be similar, prediction of a segmentation map of one slice can be enabled according to the segmentation map of an adjacent or other nearby slice. In some implementations, after a first surrogate context is obtained on a first slice, and the machine learning process may use the first surrogate context to perform a segmentation process on a second distinct slice (e.g., query set) adjacent to the first slice in the same scan. In some implementations, the machine learning process may use the surrogate context to recursively inform segmentation map predictions of subsequent query sets in the same scan.

In some implementations, the surrogate context may include any combination of the current query set, adjacent or similar sets of interest, adjacent or similar segmentation maps or user-defined annotation maps of interest, and extracted features of interest (such as extracted edge detection maps) from current, adjacent, or similar sets. In some examples, an adjacent set is a set that is directly next to the support set in the image, such that they may share a border. In some examples, a similar set is a set that may not be directly next to the support set, but instead may be from the same scan, from a different scan of the same subject, or from a different scan of a similar anatomy. Continuing the example above, after the segmentation map is generated on the second slice (e.g., a first query set), the surrogate context may be then updated to include the segmentation map of the second slice, which may be further used for performing segmentation on a third adjacent slice (e.g., a second query set).

In some implementations, the machine learning process for performing segmentation may be implemented by an artificial neural network (ANN), or other types of machine learning algorithms, e.g., random forest algorithms. In some implementations, the ANN may be a class-agnostic ANN, or another type of ANN. In some implementations, the ANN is trained to predict segmentation maps of one or more structures of interest of a new query set, or any set from the same or a similar scan of a medical image based on the surrogate context. In some examples, before inputting the surrogate context of the support set and the query set to the ANN, the ANN may be tuned or trained for segmenting a generic ROI in medical images. In some implementations, the ANN is trained to segment specific anatomical structures of interests using conventional supervised, semi-supervised, or reinforcement learning frameworks and is trained with a surrogate context that is not necessarily from a medical image.

At 208, an output is generated. In some cases, the output generated by the ANN may contain segmentation information of the query set. In some examples, the segmentation information may be in one or more forms of a segmentation map, a contour map, or in another format that delineates one or more regions of interest in the medical image. In some implementations, the output may include a segmentation map for the full medical image obtained or for a portion of the medical image. In some examples, the segmentation map identifies multiple anatomical structures or features of interest in the medical image. In some implementations, the format of the output, e.g., the segmentation map of the query set, is in accordance with the format of the input (e.g., the surrogate context, the support set, and the query set). For instance, an ANN that receives slices from a 3D volumetric scan as inputs may generate corresponding segmentation maps for slices from the 3D volumetric scan as outputs.

In some instances, the process 200 is applied iteratively or recursively over a plurality of subsequent query sets in the same medical image, for example, using the same surrogate context or an updated surrogate context on each iteration. In some instances, an output of the ANN (e.g., a segmentation map of a query set) may be further used together with the surrogate context of a support set to generate an updated surrogate context for segmenting a subsequent query set. In some instances, prior to being used as a part of the updated surrogate context, the segmentation map of the query set may be analyzed or edited for quality control purposes.

Figure 4:
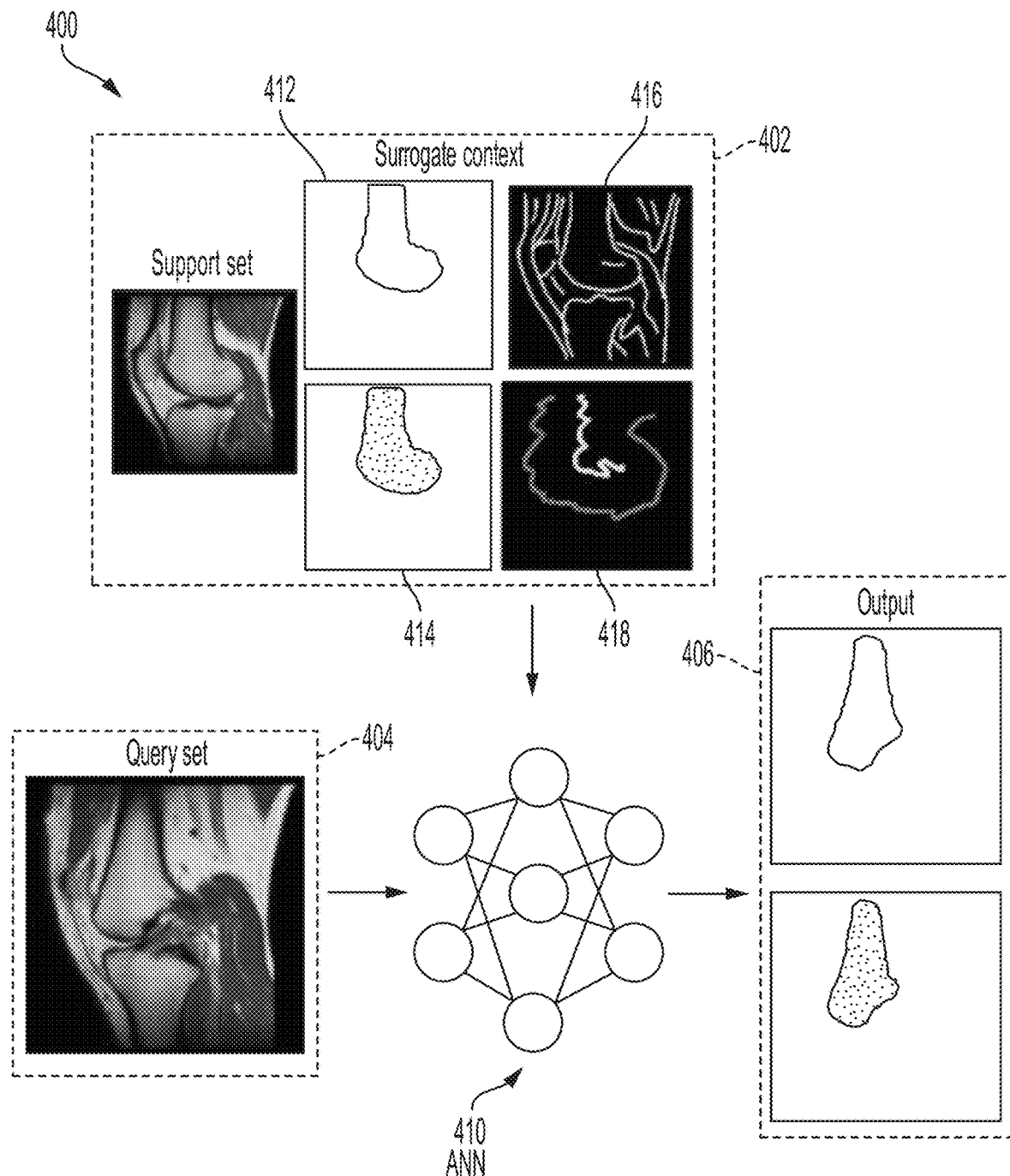
FIG. 4 is a schematic diagram of an example medical image segmentation process.

FIG. 4 is a schematic diagram of an example medical image segmentation process 400. In some examples, the process 400 may be used for segmentation of medical images generated by a medical imaging system (e.g., the medical imaging system 104 shown in FIG. 1). In some implementations, the example process 400 shown in FIG. 4 may be performed by a computer system (e.g., the computer system 102 in FIG. 1). In some cases, the example process 400 may be performed by a computer of the medical imaging system, a cloud-based computer system, a server, a server cluster, a serverless computer environment, or another type of computer system. In some cases, the process 400 may include additional or different operations, and the operations may be performed in the order shown in FIG. 4 or in another order. In some implementations, one or more of the operations in the process 400 may be repeated or iterated, performed in parallel with other operations, or handled in another manner.

At 402, a support set and a surrogate context of the support set are provided as input to an artificial neuron network (ANN) 410. The support set and the surrogate context are provided as input to the ANN to support a segmentation process on a query set. In some implementations, the support set and the query set each includes a subset of a series of images of a medical image that is generated by a medical imaging system. In some implementations, the medical image may include any type of images generated by the medical imaging system (e.g., the medical imaging system 104 as shown in FIG. 1). In some implementations, the medical image collected by the medical imaging system may include two-dimensional (2D) images, three-dimensional (3D) images, four-dimensional (4D) images or a combination thereof. In some cases, the medical images collected may include a series of related medical images, for example, a series of 2D images (e.g., slices) representing a 3D volume or a time series. In some examples, the series of slices may be collected with the aim of segmenting or delineating a specific structure or region of an imaging subject.

The surrogate context may include one or more of maps shown in FIG. 4, which can be generated as described above, for example, with respect to FIGS. 2 and 3. In the example shown in FIG. 4, the surrogate context may include a contour map 412, a segmentation map 414, or an annotation map 418 of a femur of a human knee. In some implementations, the surrogate context may include both an extracted-feature map 416 and an annotation map 418. In some examples, the extracted-feature map may be obtained by automatically detecting boundaries of features in the medical image using, for example computer vision based on image gradients or other heuristics. In some examples, the annotation map 418 may include a click drawing by a user to identify a foreground and a background. In some implementations, when both an extracted-feature map 416 and the annotation map 418 are both used as an input to the ANN, segmentation performance in terms of speed and accuracy may be improved.

At 404, a query set is provided as input to the ANN 410. In some cases, the query set includes a subset of images (one or more images) from the series of images of the medical image that were not included in the support set. In some implementations, the support set and the query set may be obtained from the same scan. In some examples, the support set and the query set are obtained from different scans. In some examples, the surrogate context and the query set may come from different medical images with different image modalities. In some instances, the support set and the query set may be determined from the medical images using an automatic method, e.g., based on a similarity metric. As shown in FIG. 4, the surrogate context, the support set, and the query set are provided as inputs to the ANN 410.

In some implementations, the ANN 410 is configured to perform a segmentation process based on the inputs, e.g., the surrogate context, the support set and the query set. In some implementations, the ANN 410 may be a class-agnostic ANN or another type of ANN. In some instances, a class-agnostic ANN may generate segmentation information, e.g., a segmentation map of the query set, in which an integer representing a region or a feature in a slice of the query set may not be permanently assigned to the region or the feature in other slices. In certain examples, the ANN 410 may be implemented as a machine-learning model that can be tuned (e.g., trained) based on training inputs to approximate unknown functions. In some instances, the ANN 410 may include a model of interconnected digital neurons that communicate and learn to approximate complex functions and generate outputs based on a plurality of inputs provided to the model. In certain instances, the ANN 410 may include one or more machine learning or deep learning algorithms. In some implementations, the ANN 410 may represent a system that implements deep learning techniques, e.g., machine learning that utilizes a set of algorithms to attempt to predict a segmentation map of a query set. In some implementations, the ANN 410 may be constructed with any variation or combination of functions that normally compose deep learning architectures such as, convolutional layers, fully-connected NN layers, recurrent layers, attention modules, and external memory mechanisms, or any other types of machine learning algorithms. In some examples, the segmentation process may be performed by another type of machine learning process such as, for example, random forest algorithms.

In some implementations, before inputting the surrogate context of the support set and the query set to the ANN 410, the ANN 410 may be tuned or trained for segmenting a generic region of interest (ROI) in medical images. In some examples, a non-linear function approximator as flexible as an ANN 410 may be used. In some implementations, the inputs to the class-agnostic ANN 410 are not limited to one type of medical image modality or structure, e.g., the support set and the query set may have different modalities or structures.

In some implementations, the ANN 410 can be trained to predict the segmentation maps of one or more structures of interest in the query set, or any set from the same or a similar scan of a medical image based on the surrogate context. In such cases, the ANN 410 may be trained to segment annotations labeled as background, foreground 1, foreground 2, . . . , foreground N. In some implementations, because the ANN 410 is trained to distinguish the class-agnostic ROI from the background, the ANN 410 can be trained using any number of segmentation data sets from varying domains (e.g., natural images, different medical image modalities, etc.) without being limited to the domain of medical images. In some implementations, the "class" of a predicted segmentation may be recovered by a user in practice when the system is implemented as a feature in a medical image processing software.

In some implementations, the ANN 410 can be trained using output data generated by conventional supervised, semi-supervised, or reinforcement learning frameworks and or can be trained with a surrogate context that is not necessarily from the domain of medical images. For instance, the ANN 410 may be trained using natural images or synthetic images and may be applied to segmentation of the specific anatomical structures of interests. In some examples, the specific anatomical structures of interests may include a femur from a CT image, tibial cartilage from an MRI image, or another type of anatomical structure.

In some implementations, the ANN 410 can be fine-tuned by adjusting weights and parameters of the ANN 410 after an initial training step. In some instances, the support set may be used to train a first ANN to determine weights of a second ANN. In some instances, the second ANN may receive the query set and use the weights determined by the first ANN for the segmentation process on the query set. In some implementations, a weight regression may be utilized by the ANN 410. In some implementations, the ANN 410 is used to predict an offset of a baseline segmentation map. For example, instead of predicting a segmentation map, vectors that regress the offset of the segmentation map of the support set can be predicted by the ANN 410.

In some implementations, the ANN 410 may be retrained by reinitializing parameters of the ANN 410 and then using a learning algorithm to learn new parameters. In some implementations, the ANN 410 may be exposed to new data without reinitializing the parameters. In some implementations, the ANN 410 could be further updated using learning algorithms that are specifically designed for online learning.

In some implementations, the ANN 410 may determine the segmented structure in the query set according to the surrogate context of the support set. In some cases, the surrogate context may provide the ANN 410 with the context necessary to generate the segmentation maps for the query set. In some examples, the ANN 410, after receiving the query set, may predict a segmentation map in various ways. For example, the ANN 410 may explicitly predict the segmentation maps or the boundaries. In some cases, the predictions of the segmentation maps or the boundaries are determined using a "deep metric embedding" method, in which the predictions are in the form of an embedding and a similarity metric is used to infer the actual prediction.

At 406, an output is generated. In some cases, the output generated by the ANN 410 may contain segmentation information of the query set. In some examples, the segmentation information may be in one or more forms of a contour map, a segmentation map, or in another format that delineates one or more regions of interest in the medical image. In some implementations, the segmentation information may include one or more segmentation maps for an image in the query set. In some examples, a segmentation map may identify one or more anatomical structures or features of interest in the image of the query set. In some implementations, formats of the output, e.g., the segmentation map, is in accordance with the format of the input (e.g., the query set, the support set and the surrogate context). For instance, an ANN 410 that receives slices from a 3D volumetric scan as inputs may generate corresponding segmentation maps for slices of the 3D volumetric scan as outputs. In the example shown in FIG. 4, the segmentation information at 406 identified by the ANN 410 includes a contour map and a segmentation map of a region of interest, e.g., a femur of a human knee, in the example image of the query set.

In some instances, the process 400 may be performed iteratively or recursively over a plurality of query sets in the same medical image, for example, using the same surrogate context and the support set, or an updated surrogate context on each iteration. In some instances, an output of a first query set may be used together with the surrogate context of the support set to generate an updated surrogate context for segmenting a subsequent second query set. In some instances, prior to being used as a part of the updated surrogate context, the first query set and its segmentation map may be analyzed or edited for quality control purposes.

Figure 5:
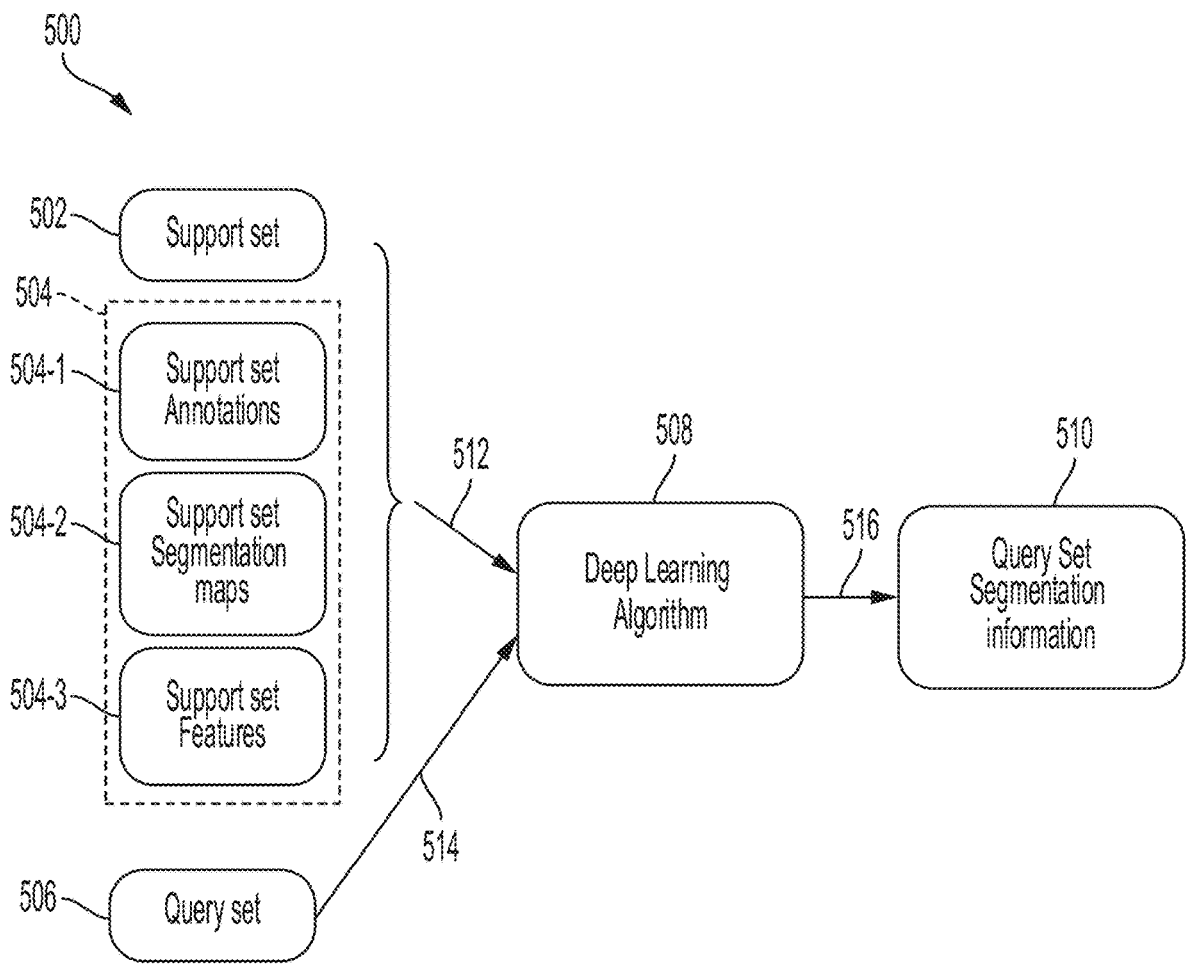
FIG. 5 is a schematic diagram of an example medical image segmentation process.

FIG. 5 is a schematic diagram of an example medical image segmentation process 500. The example process 500 shown in FIG. 5 may be performed by a computer system (e.g., by the computer system 102 in FIG. 1) to segment medical images. In some cases, the process 500 may be performed by a medical imaging system computer, a cloud-based computer system, a server, a server cluster, a serverless computer environment, or another type of computer system. In some examples, the process 500 can be used for segmentation of medical images generated by a medical imaging system (e.g., the medical imaging system 104 shown in FIG. 1). In some cases, the process 500 may include additional or different operations, and the operations may be performed in the order shown in FIG. 5 or in another order. In some implementations, one or more of the operations in the process 500 may be repeated or iterated, performed in parallel with other operations, or handled in another manner.

At 512, a support set 502 and its surrogate context 504 are provided to a deep learning algorithm 508. In some examples, the support set 502 and the surrogate context 504 are provided as input to the deep learning algorithm 508 to support a segmentation process on a query set 506. In some implementations, the support set 502 and the query set 506 each includes a subset of a series of images in a medical image that are collected by a medical imaging system (e.g., the medical imaging system 104 shown in FIG. 1) and imported to a computer system (e.g., the computer system 102 as shown in FIG. 1). In some implementations, the medical images collected by the medical image system may include two-dimensional (2D) images, three-dimensional (3D) images, four-dimensional (4D) images or a combination thereof. In some cases, the medical image collected may include a series of related medical images, for example, a series of 2D images (e.g., slices) representing a 3D volume or a time series. In some examples, the series of slices may be collected with the aim of segmenting or delineating a specific structure or region of an imaging subject.

In the example process 500 shown in FIG. 5, the surrogate context 504 of the support set 502 includes annotations 504-1, segmentation maps 504-2, and features 504-3. In some examples, the annotations 504-1 of the support set 502 may include scribbles and point clicks (e.g., an annotation map 418 as shown in FIG. 4) provided by a user (e.g., trained medical professional, technician, or other user) through a user input device of a computer system. In some examples, the features 504-3 of the support set 502 may be determined from edge detection (e.g., an extracted-feature map 416 as shown in FIG. 4). In some implementations, the surrogate context 504 may include a contour map, a key point map, coordinates of point clicks, or another format.

At 514, a query set 506 is provided to the deep learning algorithm 508. In some cases, the query set 506 may include a subset of the series of images in the medical image that were not included in the support set. In some examples, the segmentation process may be performed as described above, for example, with respect to FIGS. 2-4.

At 516, segmentation information 510 of the query set 506 are generated. In some examples, the segmentation information 510 may be in the form of a contour map, a segmentation map, or in another format that delineates one or more regions of interest in the medical image. In some implementations, the segmentation information 510 may include a segmentation map for an image or for a portion of an image in the query set. In some examples, the segmentation information 510 may identify one or more anatomical structures or features of interest in the image of the query set. In some implementations, formats of the segmentation information, e.g., the segmentation information 510 of the query set, is in accordance with the format of the input (e.g., the query set 506, the support set 502 and the surrogate context 504). For instance, a deep learning algorithm 508 that receives slices from a 3D volumetric scan as inputs may generate corresponding segmentation information for slices of the 3D volumetric scan as outputs.

Figure 6:
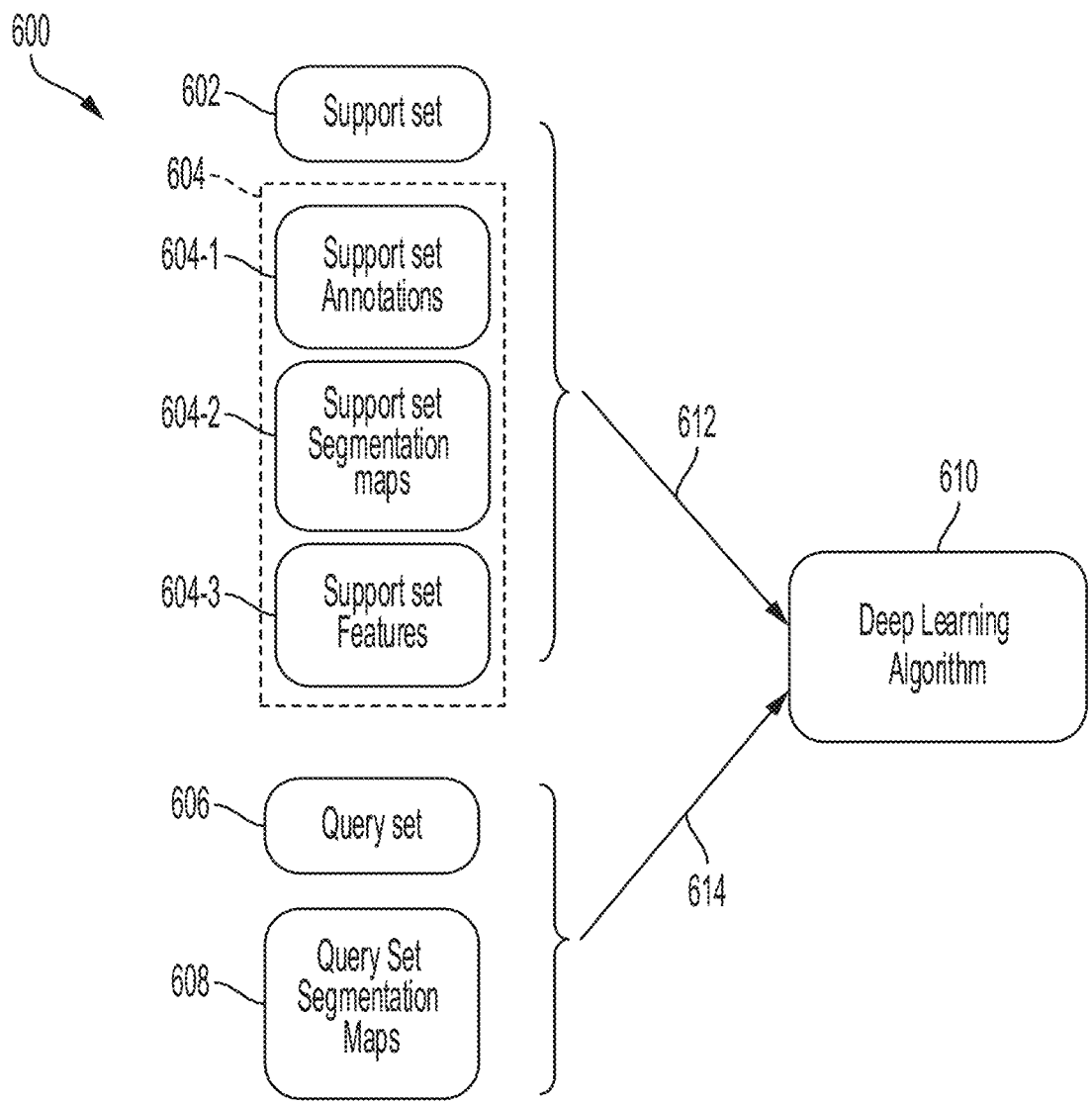
FIG. 6 is a schematic diagram of an example training process for a medical image segmentation process.

FIG. 6 is a schematic diagram of an example retraining process 600 for a deep learning algorithm 610. The example retraining process 600 shown in FIG. 6 may be performed by a computer system, for example, a medical imaging computer, a cloud-based computer system, a server, a server cluster, a serverless computer system, or another type of computer system. In some cases, the process 600 may include additional or different operations, and the operations may be performed in the order shown in FIG. 6 or in another order. In some implementations, one or more of the operations in the process 600 may be repeated or iterated, performed in parallel with other operations, or handled in another manner.

At 612, a support set 602 of a medical image and a surrogate context 604 of the support set 602 are provided to a deep learning algorithm 610. In some examples, the support set 602 and the surrogate context 604 are provided as input to the deep learning algorithm 610 to support a retraining process of the deep learning algorithm 610. In some implementations, the support set 602 and the query set 606 each includes a subset of a series of images in the medical image that are collected by a medical imaging system (e.g., the medical imaging system 104 shown in FIG. 1) and imported to a computer system (e.g., the computer system 102 shown in FIG. 1). In some implementations, the medical image may include any type of medical images generated by the medical imaging system. In some implementations, the medical image collected by the medical image system may include two-dimensional (2D) images, three-dimensional (3D) images, four-dimensional (4D) images or a combination thereof. In some cases, the medical image collected by the medical imaging system may include a series of related medical images, for example, a plurality of 2D images (e.g., slices) representing a 3D volume or a time series. In some examples, the plurality of slices may be collected with the aim of segmenting or delineating a specific structure or region of an imaging subject. In some cases, the surrogate context 604 may be generated as described above.

In the example process 600 shown in FIG. 6, the surrogate context 604 of the support set 602 includes annotations 604-1, segmentation maps 604-2, and features 604-3. In some examples, the annotations 604-1 of the support set may include scribbles and point clicks (e.g., an annotation map 418 as shown in FIG. 4) provided by a user (e.g., trained medical professional, technician, or other user) through a user input device of a computer system. In some examples, the features 604-3 of the support set may be determined from edge detection (e.g., an extracted-feature map 416 as shown in FIG. 4). In some implementations, the surrogate context 604 may include a contour map, a key point map, coordinates of point clicks, or another format.

At 614, the query set 606 and segmentation maps 608 of the query set 606 are provided to the deep learning algorithm 610. In some cases, the query set 606 includes a subset of the series of images in the medical image that were not included in the support set 602. In some implementations, the support set 602 and the query set 606 may be obtained from the same scan. In some instances, the support set 602 and the query set 606 are obtained from different scans. In some examples, the support set 602 and the query set 606 may come from different medical images with different image modalities. In some cases, the support set 602 and the query set 606 may be determined using an automatic method, e.g., based on a similarity metric.

In some implementations, the segmentation maps 608 of the query set 606 may be obtained as an output from a previous deep learning process as shown in FIGS. 2, 4 and 5. In some instances, the deep learning process may use the deep learning algorithm 610, which may be implemented by an artificial neural network (ANN). In some implementations, the segmentation maps 608 may include one or more segmentation maps for an image or for a portion of an image in the query set 606. In some examples, the segmentation map 608 of the query set 606 identifies multiple anatomical structures or features of interest in the images of the query set 606. In some implementations, the format of the segmentation maps 608 of the query set 606, is in accordance with the format of the surrogate context 604 of the support set 602 and the query set.

In some cases, the support set 602, the surrogate context 604, the query set 606 and the segmentation maps 608 of the query set 606 are provided to the deep learning algorithm 610 for retraining purposes. In some cases, the retraining process 600 is performed in an iterative or recursive manner, in which segmentation results obtained on subsequent query sets can be further used as inputs to retrain the deep learning algorithm 610. In some cases, the process 600 may be used in a fine-tuning process of the deep learning algorithm 610.

In a general aspect, medical images are segmented by a medical image segmentation system.

In a first example, a medical image segmentation method includes obtaining a medical image comprising a series of images; obtaining a surrogate context based on a support set of images; identifying a query set of images; providing the surrogate context, the support set of images and the query set of images as inputs to a machine learning process; and segmenting the query set by operation of the machine learning process executed on a computer system, wherein executing the machine learning process produces segmentation information of the query set. The support set of images includes a first subset of the series of images and the query set of images includes a second subset of the series of images.

Implementations of the first example may include one or more of the following features. The medical image segmentation method further includes selecting the support set of images and the query set of images from the series of images according to a pre-determined similarity metric. The support set includes a single two-dimensional image and the surrogate context includes a two-dimensional segmentation map for the single two-dimensional image. The query set of images includes the support set of images. Each of the support set and the query set includes a respective three-dimensional image. The surrogate context includes at least one of a segmentation map, a contour map, an extracted feature, a key point map, an annotation, or coordinates of point clicks. The surrogate context is generated by manual annotation or a semi-automatic process. Executing the machine learning process includes operating an artificial neural network.

Implementations of the first example may include one or more of the following features. The query set includes a first query set and the segmentation information includes a first segmentation map, and the medical image segmentation method further includes: after segmenting the first query set, updating the surrogate context with the first segmentation map of the first query set; identifying a second query set of images; providing the updated surrogate context and the second query set of images as inputs to the machine learning process; segmenting the second query set by operation of the machine learning process executed on the computer system. The second query set of images includes a third subset of the series of images. Executing the machine learning process produces a second segmentation map of the second query set. The medical image includes a volumetric image, and the series of images includes a series of slices obtained by a series of scans. The support set is a single slice of the volumetric image. A magnetic resonance imaging (MRI) system is used for generating the medical image.

In a second example, a medical image segmentation system includes a medical imaging system to generate a medical image with a series of images and a computing system includes one or more processors and a computer-readable medium storing instructions that are operable when executed by the one or more processors to perform one or more operations of the first example.

In a third example, a non-transitory computer-readable medium storing instructions that are operable when executed by data processing apparatus to perform operations of the first example.

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of embodiments have been described. Nevertheless, it will be understood that various modifications can be made. Accordingly, other embodiments are within the scope of the following claims.

What is claimed is:

1. A medical image segmentation method comprising:
   obtaining a medical image comprising a series of images;
   obtaining a surrogate context based on a support set of images, the support set of images comprising a first subset of the series of images;
   identifying a query set of images, the query set of images comprising a second subset of the series of images;
   providing the surrogate context, the support set and the query set as inputs to a machine learning process; and
   segmenting the query set by operation of the machine learning process executed on a computer system, wherein executing the machine learning process produces segmentation information of the query set.

2. The method of claim 1, comprising selecting the support set and the query set from the series of images according to a pre-determined similarity metric.

3. The method of claim 1, wherein the support set comprises a single two-dimensional image and the surrogate context comprises a two-dimensional segmentation map for the single two-dimensional image.

4. The method of claim 1, wherein the query set comprises the support set.

5. The method of claim 1, wherein each of the support set and the query set comprises a respective three-dimensional image.

6. The method of claim 1, wherein the surrogate context comprises at least one of a segmentation map, a contour map, an extracted feature, a key point map, an annotation, or coordinates of point clicks.

7. The method of claim 1, wherein the surrogate context is generated by manual annotation or a semi-automatic process.

8. The method of claim 1, wherein executing the machine learning process comprises operating an artificial neural network.

9. The method of claim 1, wherein the query set comprises a first query set, the segmentation information comprises a first segmentation map, and the method further comprises:
   after segmenting the first query set, updating the surrogate context to obtain an updated surrogate context comprising the first segmentation map of the first query set;
   identifying a second query set of images, the second query set of images comprising a third subset of the series of images;
   providing the updated surrogate context and the second query set as inputs to the machine learning process;
   segmenting the second query set by operation of the machine learning process, wherein executing the machine learning process produces a second segmentation map of the second query set.

10. The method of claim 1, wherein the medical image comprises a volumetric image, and the series of images comprises a series of slices obtained by a series of scans.

11. The method of claim 10, wherein the support set is a single slice of the volumetric image.

12. The method of claim 1, comprising generating the medical image by operation of a magnetic resonance imaging (MRI) system.

13. A system comprising:
   a medical imaging system configured to generate a medical image comprising a series of images; and
   a computer system comprising:
      one or more processors; and
      memory storing instructions that, when executed, cause the one or more processors to perform operations comprising:
         obtaining the medical image from the medical imaging system;
         obtaining a surrogate context based on a support set of images, the support set of images comprising a first subset of the series of images;
         identifying a query set of images, the query set of images comprising a second subset of the series of images;
         providing the surrogate context, the support set and the query set as inputs to a machine learning process; and segmenting the query set by operation of the machine learning process, wherein executing the machine learning process produces segmentation information of the query set.

14. The system of claim 13, wherein the operations further comprise selecting the support set and the query set from the series of images according to a pre-determined similarity metric.

15. The system of claim 13, wherein the support set comprises a single two-dimensional image and the surrogate context comprises a two-dimensional segmentation map for the single two-dimensional image.

16. The system of claim 13, wherein the query set comprises the support set.

17. The system of claim 13, wherein each of the support set and the query set comprises a respective three-dimensional image.

18. The system of claim 13, wherein the surrogate context is generated by manual annotation or a semi-automatic process.

19. The system of claim 13, wherein executing the machine learning process comprises operating an artificial neural network.

20. The system of claim 13, wherein the query set comprises a first query set, the segmentation information comprises a first segmentation map, and the operations further comprise:
   after segmenting the first query set, updating the surrogate context to obtain an updated surrogate context comprising the first segmentation map of the first query set;
   identifying a second query set of images, the second query set of images comprising a third subset of the series of images;
   providing the updated surrogate context and the second query set as inputs to the machine learning process;
   segmenting the second query set by operation of the machine learning process executed on the computer system, wherein executing the machine learning process produces a second segmentation map of the second query set.

21. The system of claim 13, wherein the medical image comprises a volumetric image, and the series of images comprises a series of slices obtained by a series of scans, and the support set of images is a single slice of the volumetric image.

22. The system of claim 13, wherein the medical imaging system comprises a magnetic resonance imaging (MRI) system.

23. A non-transitory computer-readable medium storing instructions that are operable when executed by data processing apparatus to perform operations comprising:
   obtaining a medical image comprising a series of images;
   obtaining a surrogate context based on a support set of images, the support set of images comprising a first subset of the series of images;
   identifying a query set of images, the query set of images comprising a second subset of the series of images;
   providing the surrogate context, the support set and the query set as inputs to a machine learning process; and
   segmenting the query set by operation of the machine learning process, wherein executing the machine learning process produces segmentation information of the query set.

24. The non-transitory computer-readable medium of claim 23, wherein the operations further comprise selecting the support set and the query set from the series of images according to a pre-determined similarity metric.

25. The non-transitory computer-readable medium of claim 23, wherein the support set comprises a two-dimensional image and the surrogate context comprises a two-dimensional segmentation map for a single two-dimensional image.

26. The non-transitory computer-readable medium of claim 23, wherein the query set comprises the support set.

27. The non-transitory computer-readable medium of claim 23, wherein each of the support set and the query set comprises a three-dimensional image.

28. The non-transitory computer-readable medium of claim 23, wherein operating the machine learning process comprises operating an artificial neural network.

29. The non-transitory computer-readable medium of claim 23, wherein the query set comprises a first query set, the segmentation information comprises a first segmentation map, and the operations further comprise:
   after segmenting the first query set, updating the surrogate context to obtain an updated surrogate context comprising the first segmentation map of the first query set;
   identifying a second query set of images, the second query set of images comprising a third subset of the series of images;
   providing the updated surrogate context and the second query set as inputs to the machine learning process;
   segmenting the second query set by operation of the machine learning process, wherein executing the machine learning process produces a second segmentation map of the second query set.

30. The non-transitory computer-readable medium of claim 23, wherein the medical image comprises a volumetric image, and the series of images comprises a series of slices obtained by a series of scans, and the support set of images is a single slice of the volumetric image.

* * * * *